US 8,504,136 B1

(12) United States Patent
Sun et al.

(10) Patent No.: US 8,504,136 B1
(45) Date of Patent: Aug. 6, 2013

(54) SEE-THROUGH ABDOMEN DISPLAY FOR MINIMALLY INVASIVE SURGERY

(75) Inventors: Yu Sun, Tampa, FL (US); Richard D. Gitlin, Tampa, FL (US); Adam Anderson, Tampa, FL (US); Alexander Rosemurgy, Tampa, FL (US); Sharona Ross, Tampa, FL (US)

(73) Assignee: University of South Florida, Tampa, FL (US)

(*) Notice: Subject to any disclaimer, the term of this patent is extended or adjusted under 35 U.S.C. 154(b) by 391 days.

(21) Appl. No.: 12/899,076

(22) Filed: Oct. 6, 2010

Related U.S. Application Data (60) Provisional application No. 61/249,075, filed on Oct. 6, 2009.

(51) Int. Cl.
*A61B 5/05* (2006.01)

(52) U.S. Cl.
USPC .......................................... 600/407; 600/476

(58) Field of Classification Search
USPC .......................................... 600/407, 427, 476
See application file for complete search history.

(56) References Cited

U.S. PATENT DOCUMENTS

| | | | | |
|---|---|---|---|---|
| 5,715,836 A | * | 2/1998 | Kliegis et al. | 600/425 |
| 5,772,593 A | * | 6/1998 | Hakamata | 600/407 |
| 5,999,840 A | * | 12/1999 | Grimson et al. | 600/424 |
| 6,517,484 B1 | * | 2/2003 | Wilk et al. | 600/437 |
| 6,571,118 B1 | * | 5/2003 | Utzinger et al. | 600/476 |
| 7,567,833 B2 | * | 7/2009 | Moctezuma De La Barrera et al. | 600/424 |
| 2007/0038118 A1 | * | 2/2007 | DePue et al. | 600/476 |
| 2008/0004525 A1 | * | 1/2008 | Goldman et al. | 600/425 |
| 2008/0051773 A1 | * | 2/2008 | Ivanov et al. | 606/12 |
| 2009/0163809 A1 | * | 6/2009 | Kane et al. | 600/443 |
| 2010/0191124 A1 | * | 7/2010 | Prokoski | 600/473 |

OTHER PUBLICATIONS

Fuchs, H. et al. Augmented Reality Visualization for Laparoscopic Surgery. Lecture Notes in Computer Science. Medical Image Computing and Computer-Assisted Intervention—MICCAI'98, 1998, vol. 1496, pp. 934-943.

Grimson, E. et al. Clinical Experience with a High Precision Image-guided Neurosurgery System. Lecture Notes in Computer Science. Medical Image Computing and Computer-Assisted Intervention—MICCAI'98, 1998, vol. 1496, pp. 63-73.

Blackwell, M. et al. An Image Overlay System for Medical Data Visualization. Lecture Notes in Computer Science. Medical Image Computing and Computer-Assisted Intervention—MICCAI'98, 1998, vol. 1496, pp. 232-240.

Hayashibe, M. et al. Data-Fusion Display System with Volume Rendering of Intraoperatively Scanned CT Images. Lecture Notes in Computer Science. Medical Image Computing and Computer-Assisted Intervention—MICCAI, 2005, vol. 3750, pp. 559-566.

(Continued)

*Primary Examiner* — Jonathan Cwern
(74) *Attorney, Agent, or Firm* — Michele L. Lawson; Jeremy Spier; Smith & Hopen, P.A.

(57) ABSTRACT

This invention is in the domain of minimally invasive surgery and is a method and apparatus that transforms and displays images of internal organs and tissues taken from internally located imaging devices on external skin. The image displayed on the skin aligns with the actual physical location, orientation, and size of the internal organs and tissues in a way that viewers have the perception that the skin is transparent. This method and apparatus enables surgeons to have the same hand-eye coordination as in an open surgery during a minimally invasive surgery.

20 Claims, 10 Drawing Sheets

OTHER PUBLICATIONS

Nicolau, S. A. et al. A Complete Augmented Reality Guidance System for Liver Punctures: First Clinical Evaluation. Lecture Notes in Computer Science. Medical Image Computing and Computer-Assisted Intervention—MICCAI, 2005, vol. 3749, pp. 539-547.

Fischer, G. S. et al. MRI Image Overlay: Applications to Arthrography Needle Insertion. Medicine Meets Virtual Reality 14. IOS Press, 2006, pp. 150-155.

Marmurek, J. et al. Image-guided Laser Projection for Port Placement in Minimally Invasive Surgery. Studies in Health Technology and Informatics. 2006, vol. 119, pp. 367-372.

Hoppe, H. et al. Projector-based Visualization for Intraoperative Navigation: First Clinical Results. International Congress Series 1256, 2003, p. 771.

Hoppe, H. et al. A Clinical Prototype System for Projector-based Augmented Reality: Calibration and Projection Methods. CARS 2002; Computer Assisted Radiology and Surgery: Proceedings of the 16th International Congress and Exhibition Paris, Jun. 26-29, 2002.

* cited by examiner

SEE-THROUGH ABDOMEN DISPLAY FOR MINIMALLY INVASIVE SURGERY

CROSS REFERENCE TO RELATED APPLICATIONS

This application claims priority to currently pending U.S. provisional patent application No. 61/249,075, entitled "SEE-THROUGH ABDOMEN DISPLAY FOR MINIMALLY INVASIVE SURGERY," filed on Oct. 6, 2009, the contents of which are hereby incorporated by reference.

BACKGROUND OF THE INVENTION

1. Field of the Invention

This invention relates to the field of minimally invasive surgery (MIS). More specifically, it relates to a method of performing MIS by projecting images of internal organs, tissues, and surgical tools externally on the skin of a patient to create a virtual effect that the skin is transparent.

2. Description of the Prior Art

MIS utilizes small incisions in the body for the placement and manipulation of surgical equipment. MIS has been widely adapted and performed as an alternative to open surgery because it minimizes trauma, shortens hospitalizations, and increases recovery time. In 2009, the global market for MIS equipment was roughly US$15 billion with nearly US$1.7 billion spent specifically on endoscopic cameras and monitoring systems.

While MIS provides many benefits, it often takes longer to complete than equivalent open surgeries. In particular, MIS is hindered by limited viewpoints and insertion points, inconsistent and unclear orientation of video, and limited touch sensing and hand motion due to long-stick surgical tools. As a result, MIS requires significantly more training than regular open surgery, which prevents or discourages many surgeons to master the skills for MIS, especially in remote and developing regions or less-than-ideal surgical venues.

Several techniques have been developed to overcome these limitations. For example, the da Vinci® Integrated Surgical Robotic System is a high-end minimally invasive surgery robot. Hand and wrist motions of a surgeon are mapped to a robot hand motion at the da Vinci® system, and an image from an endoscope at the patient terminal is displayed on a surgeon's console. With two cameras integrated in one endoscope, the surgeons can see some level of stereo. The major benefit of the da Vinci® system is the hand-eye coordination presents the MIS as an open surgery from the surgeon's point of view.

The da Vinci® system, however, is very expensive and requires multiple incisions for the robotic arms to perform the operation. Moreover, the da Vinci® system has unwieldy robotics arms that limit its application; for example, the robotics arms are too big to insert tools near one another and have conflicts with other surgical tools during procedures.

In both traditional MIS and robotic aided MIS, the image displayed to the surgeons is via endoscopes. The state of the art commercial videoscopes (i.e. laparoscopes, endoscopes) for MIS have, and are encumbered by, cabling for power, video, and a xenon light source inside a semi-flexible or rigid mechanical rod. Many surgeons have expressed their disappointment with the fundamental limitations of these scopes based on their experience with hundreds of MIS operations. Though quite good in image quality, these videoscopes are cumbersome and require a point of access into the patient, either through a separate incision or through a separate trocar site in a multitrocar access port. The videoscope cables for light, video image, and power clutter and consume space in the operative field. They also require supporting manpower in the operating room to hold the scope and redirect it as indicated to maintain consistent and stable views of the operation being undertaken. Some developing approaches to intracavity visualization bypass the rod-lens approach of conventional videoscopes but the resulting video platforms still maintain a significant spatial presence within the operating cavity and require points of access (e.g. incisions and/or trocars) to link power and video images. In addition, the limitation of the viewpoint and view angle of the rigid endoscope is a handicap for surgeons. The misinterpretation of the image orientation on an overhead monitor also poses a significant problem to the hand-eye coordination for the surgeons and requires great skills and train to master and compensate.

Various approaches for visualization in image-guided interventions have been proposed to achieve "seeing through" effect by applying the concept of augmented reality. Augmented reality enables the surgeons to focus on the surgical site without dividing his or her attention between the patient and a separate monitor and provides hand-eye coordination as the surgeon observes the operation room. A CT image of a patient overlayed with the patient and appearing at the location of the actual anatomy is an example of augmented reality. Usually the location of the surgery tool is tracked and graphically drawn as a virtual tool and displays on the CT or other images based on the tracking to guide surgeons to operate. If the mapping does not align correctly with the patient and the surgical tool, the visualization can be dangerous. It is very challenging to achieve satisfactory accurate alignment between the tracking data and the image since it requires precise models of the patient and models of instruments.

What is needed is a method of performing MIS by projecting images of internal organs and tissues externally on the skin of a patient to create a virtual effect that the skin is transparent. Such a method would not encounter the difficult instrument mapping and alignment problem of the prior art because it captures the surgical anatomy and the surgical instrument at the same time and in the same frame.

However, in view of the prior art considered as a whole at the time the present invention was made, it was not obvious to those of ordinary skill in the art how the limitations of the art could be overcome.

SUMMARY OF INVENTION

The invention is a method and apparatus for transforming and displaying images of internal organs, tissues, and surgical tools taken from internally located imaging devices on external skin. The image displayed on the skin aligns with the actual physical location, orientation, and size of the internal organs, tissues, and surgical tools in a way that viewers have the perception that the skin is transparent. This method and apparatus enables surgeons to have the same hand-eye coordination as in an open surgery.

Generally speaking, the invention includes a plurality of micro-cameras disposed inside a patient's body that transfer wireless high-definition video images of an in vivo surgical area. The images are projected on the skin of the patient to create a virtual effect that the skin is transparent. The projection is compensated for geometry and color distortion. A surgeon-camera-interaction system allows surgeons to control their viewpoint with gesture recognition and finger tracking.

The method of projecting images of internal organs and tissues externally on the skin of a patient to create a virtually transparent effect, includes the steps of: (1) locating a plurality of imaging devices inside a patient's body, the plurality of imaging devices each providing images to a CPU; (2) processing the images from the plurality of imaging devices; (3) projecting the images externally on the skin of the patient, wherein the images are morphed together to create a virtual effect that the skin is transparent; and (4) correcting the projection of the images for geometry and color distortion, whereby a surgeon can operate as if they are looking directly into the body cavity through a transparent epidermis and tissue layer.

In an embodiment, the method further includes the step of aligning the images projected on the skin of the patient with the actual physical location, orientation, and size of the internal organs, tissues, and surgical tools in a way to create a virtual effect that the skin is transparent.

In an embodiment, the method further includes the step of providing a view morphing algorithm for processing the images from the plurality of imaging devices into a single image according to a user specified virtual viewpoint.

In an embodiment, the method further includes the step of projecting the images externally on the skin of the patient to create a 3D effect.

In an embodiment, the method further includes the step of modifying the projection of the images when the surgeon gestures to do so.

In an embodiment, the method further includes the steps of tracking the location of the surgeon's viewpoint and adjusting the projection in response to the surgeon's viewpoint so that the surgeon can operate as if the surgeon is looking directly into the body cavity as in an open surgery.

In an embodiment, video images taken from several internal cameras are transformed to one or two video displays so that they appear as though they were taken from virtual cameras from the surgeon's point of view. The viewpoint of the surgeons is tracked with tracking devices. If the camera locations are known, the transformation between the video from cameras and the virtual cameras can be computed with existing image mosaic techniques and view morphing techniques such as image backprojection. If the camera locations cannot be obtained, the transformation can be computed and the new videos can be generated with feature-based image mosaic and view morphing. To have high quality video, techniques such as global registration, contrast adjustment, and feathering can be applied. If stereo video is preferred, videos from two parallel viewpoints are generated.

The videos can be projected on many different surfaces for different setups. For example, the videos can be directly projected on the skin of the external abdomen wall for Laparo-Endoscopic Single Site (LESS) surgery. In this case, the geometry of abdomen wall and skin color will distort the image. The distortion is corrected with through image processing. Ideally, the image rendered on the abdomen wall or other surfaces with the projector will have the same pixel value as a surgeon sees in open surgery.

Accordingly, it is an objective of this invention to provide a cyber-physical system capable of displaying the in vivo surgical area directly onto a patient's skin in real-time.

It is also an object of the claimed invention to enable a surgeon to focus on the surgical site without dividing his or her attention between a patient and a separate monitor.

It is a further object of the claimed invention to provide the visual benefits of open-cavity surgery without all the associated risks to the patient.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
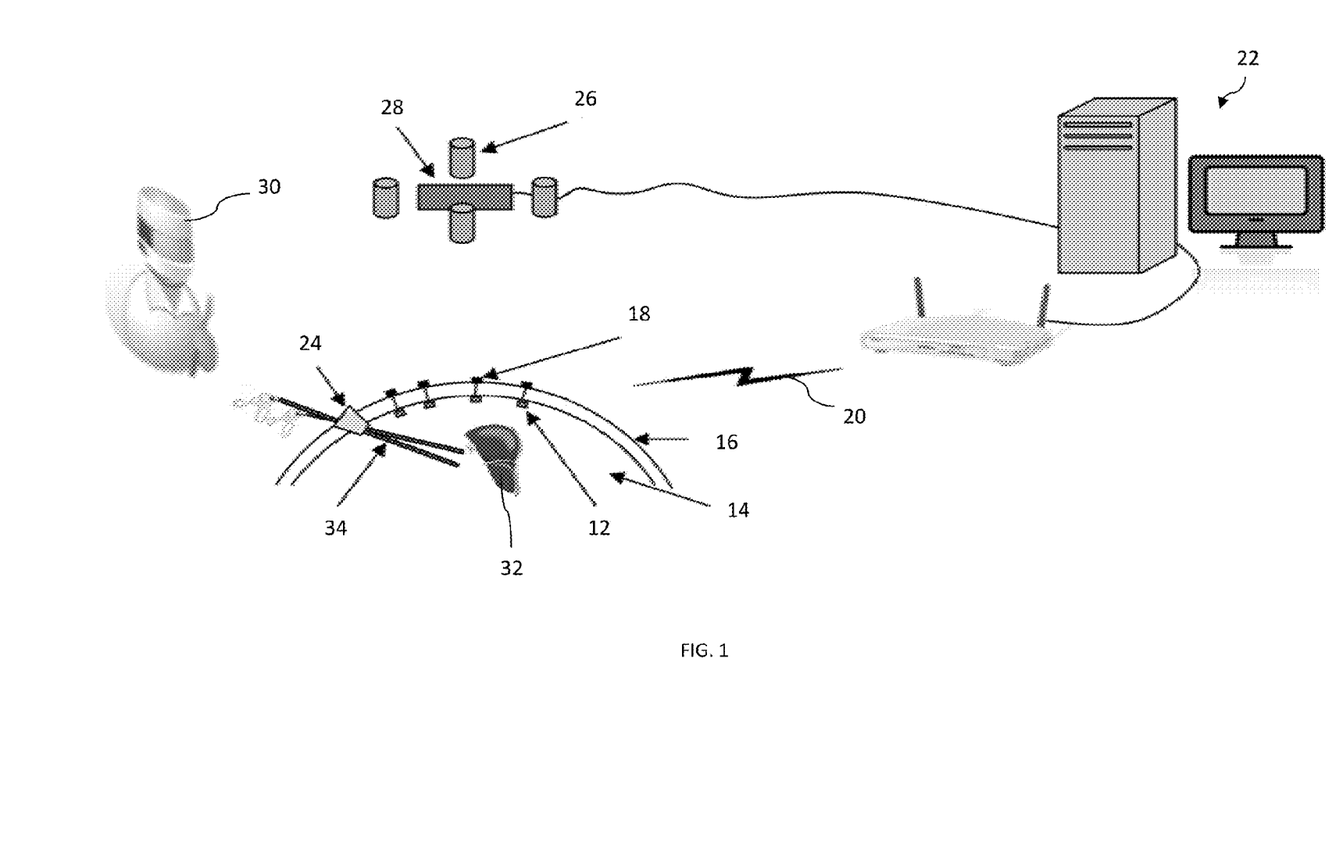
FIG. 1 is a schematic drawing of an embodiment of the claimed invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention In an embodiment, as depicted in FIG. 1, the claimed invention includes a plurality of wireless camera modules 12 that are inserted and retreated into a body cavity of interest 14 with a surgery gripper. The tiny wireless camera modules 12 are anchored around the cavity of interest 14 and provide a large view of visual feedback. The feedback is processed in real-time and displayed via projectors 26 on the human body in alignment with the physical cavity of interest 14 and provides a virtually transparent effect so that a surgeon can operate a MIS/LESS procedure with the view of an open surgery, but far less invasively.

One of the major advantages of the open surgery over MIS is the natural perception available to a surgeon. The millimeter-scale, self-contained, cable-free camera modules alleviate field of view loss when undertaking operations with conventional videoscopic instrumentation. Since adding multiple such camera madules within the body is not constrained by the limited number of incisions or trocar 24 sites, due to their serial insertion, surgeons can add several camera modules as space dictates within the operating cavity 14 without increasing the overall invasiveness of the procedure or without adding to the clutter of the operative field. Multiple camera madules provide a surgeon with additional real-time imaging of a broader operative field, provide visual depth to the operative field, expedite completion of operations, and promote patient safety.

The invention is an integration of several novel technologies to create a truly cyber-physical system. FIG. 1 illustrates a system overview that is composed of a novel wireless video camera module network 12, a panoramic virtual view generating and projecting system 26, a distortion feedback stereo camera 28, and a novel surgeon-camera-interaction (SCI) technique 30 to allow surgeons to control the view and display on the body of the internal organs 32, tissues, and surgical tools 34.

Camera System

Figure 2:
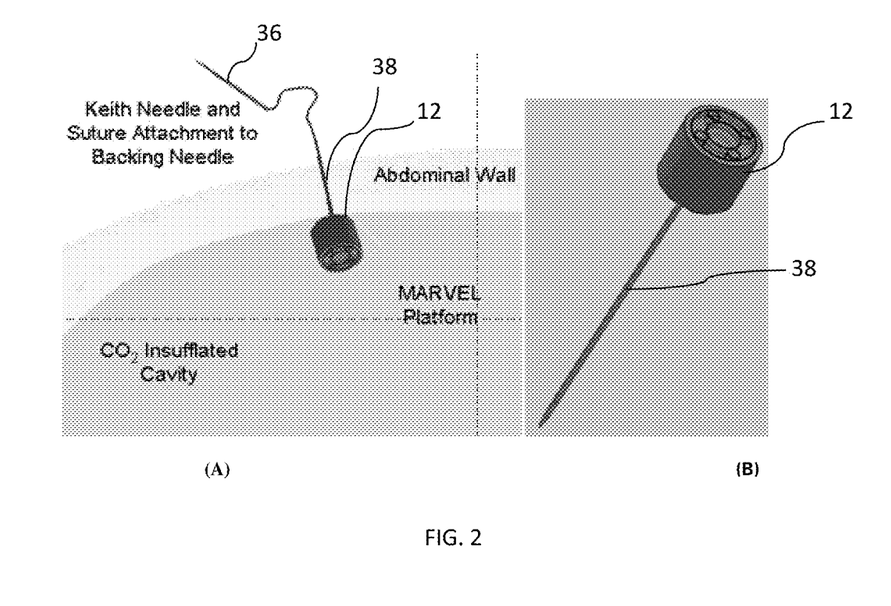
FIG. 2A illustrates a camera unit disposed within a body cavity.
FIG. 2B illustrates a camera unit.

Millimeter-scale Miniature and Anchored Remote Videoscope for Expedited Laparoscopy (MARVEL) is a wireless camera network system that uses a number of millimeter diameter wireless videoscopes that are attached in multitude inside the cavity wall through one incision site without occupying a port during surgeries. As illustrated in FIGS. 1-2B, a number of tiny wireless cameras 12 are anchored through the cavity of interest 12 through abdominal wall 16 with Keith needles 36 and held by needle holders 38 that also provide power. During LESS operations, for example, a number of the wireless camera units are attached inside the patient within the body cavity of interest (e.g. abdominal, pelvic, thoracic) as dictated by the surgeon to provide a wide view with high resolution.

As depicted in FIG. 1, the wireless link transmits a video signal 20 to a computer 22 without cable(s), which enables the MARVEL camera system 12 for use in MIS/LESS surgeries by adhering to the concept of only a single incision trocar 24 and not occupying a port. The Keith needles 38 do not leave a scar. MARVEL platforms may be disposable/recyclable to avoids numerous issues which plague conventional videoscopes today, including durability and repair costs, high initial (i.e. purchasing) costs, and sterilization and infection control.

The MARVEL cameras are serially inserted and attached within the abdomen, or other operating locale, via a tiny Keith needle that protrudes through the biological tissue layers and is fixed outside the body (as depicted in FIG. 2A). As power is one of the scarcest resources for the device, the Keith needle is dual purpose and is used to power the camera module, while an internal wireless board is used to send the video signal to a receiver unit in the operating room. Another board contained within the MARVEL module provides a light source with the necessary luminosity for precision cutting. Different sized modules are used for different requirements (e.g. resolution).

Panoramic Virtual View Generating and Projecting System

Figure 3:
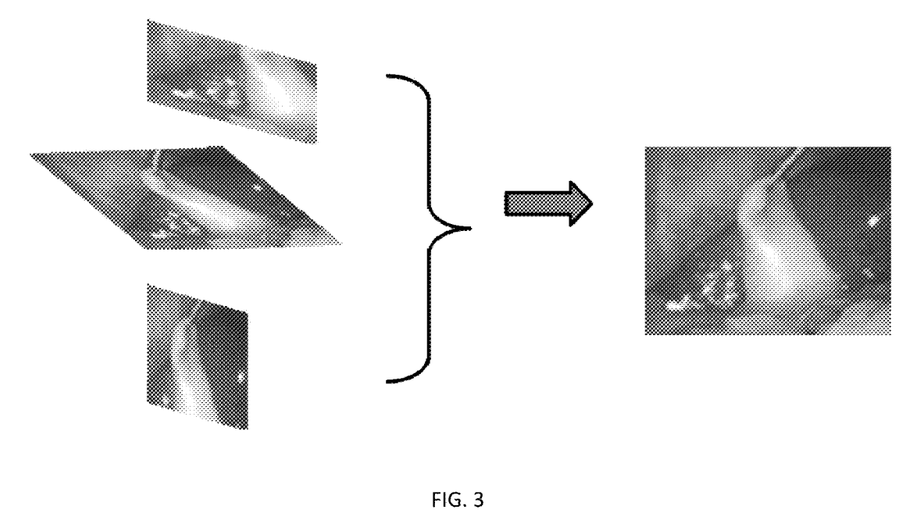
FIG. 3 illustrates how several camera angles are morphed together to form a single image.

The number of videos from different cameras looking at the cavity of interest from different viewing points is morphed together with partial overlapping areas to create a seamless panoramic video with a widened field-of-view (FOV) with a high resolution. As depicted in FIG. 3, image registration techniques, such as Scale Invariant Feature Transform (SIFT), are used and descriptor-based matching techniques to automatically compute optimal global alignment for the mosaicing of videos from different cameras. If the micro-cameras are calibrated and tracked, the mosaicing can be computed with the help of the camera intrinsic and extrinsic parameters. The panoramic virtual view generating system also prepares the mosaics for projection on any convenient viewing angle. A digital zoom option also is also provided on the mosaics.

Figure 4:
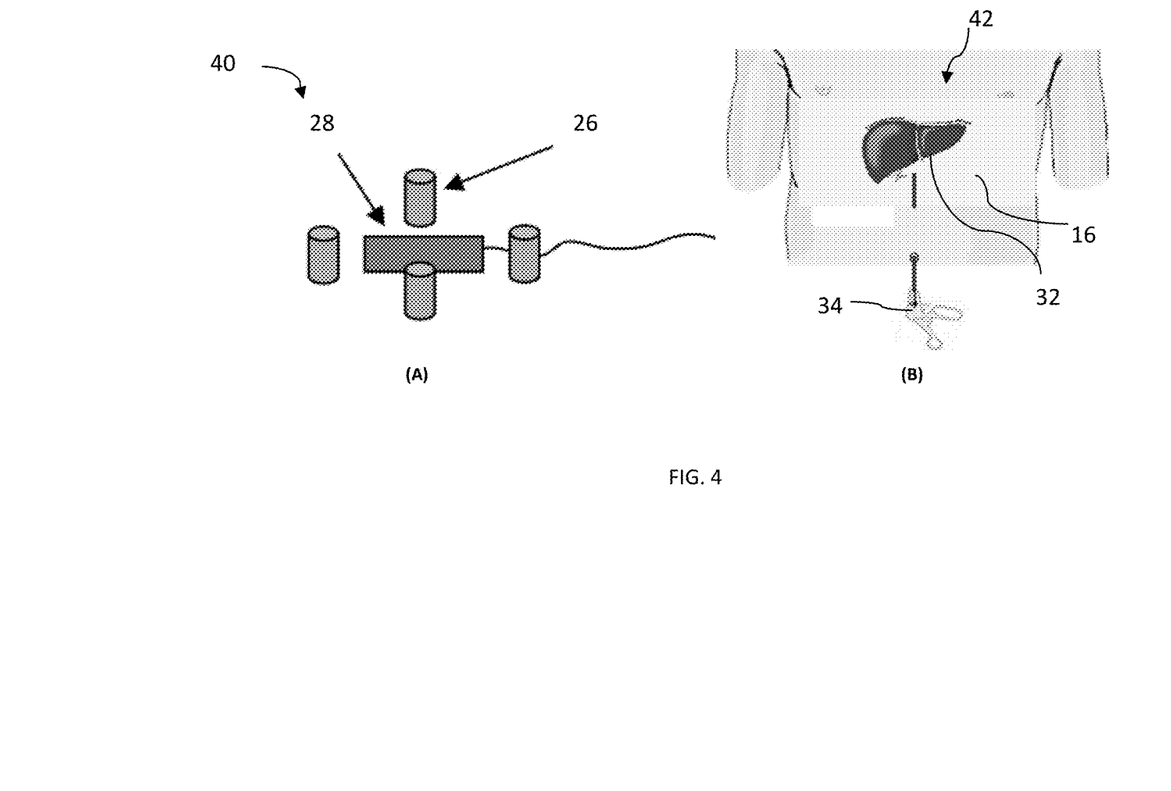
FIG. 4A illustrates a projector camera system.
FIG. 4B illustrates an image projected onto a body.

As depicted in FIG. 4A, the dynamic view projection system 40 contains four HD projectors 26 and one stereo camera 28. Four 1080i HD projectors 26 are arranged at the vertex of a square to provide max cover of projection area with limited distortion. Before being fed into the projectors, the panoramic video is processed to prevent color or geometrical distortion for the convex abdomen surface with the feedback from the Point Grey Bumblebee stereo camera 28. The stereo camera 28 provides a visual feedback for projection distortion compensation and tracks the locations of the camera units. The video 42 is then projected on the external abdomen wall 16 and align with the internal organs 32 and tools 34 to create a transparent effect, as shown in FIG. 4B.

Surgeon Camera Interaction (SCI) System

Figure 5:
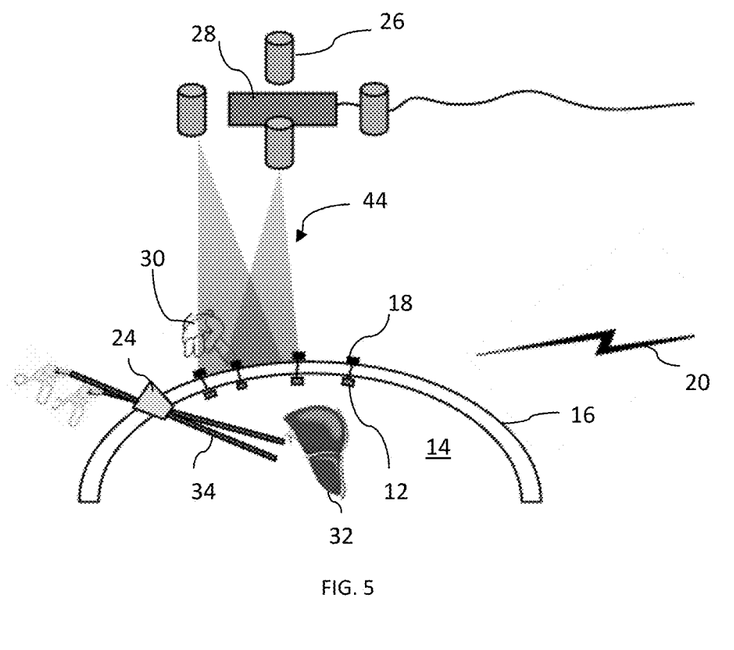
FIG. 5 illustrates how a surgeon can interact with a camera network and specify a viewing point by tapping a finger at a camera holder or an area between cameras.

A large panoramic video is displayed on the external wall after distortion compensation. It provides a panoramic overview that is useful for surgeons to localize the cavity of interest and surgical tools. Sometimes, however, it is unnecessary and even distractive to see all areas. Accordingly, a surgeon may want to concentrate on a specific area. A surgeon-camera-interface allows a surgeon to specify 30 a desired viewing point so that a narrow but concentrated view is displayed 44 at the exact spot on the exterior of the abdomen wall 16 to align with the internal cavity of interest 14, as depicted in FIG. 5.

A surgeon can use one of their fingers to touch the camera holder to tell the projector system to display video from that camera. In addition, when a surgeon taps on an area between cameras, the system will display a virtual view from that viewpoint.

It is not necessary to track the surgical instruments or align them with the mapping image since the system captures the surgical anatomy and the surgical instrument at the same time and in the same frame, which avoids the difficult instrument mapping and alignment problem. The system enables surgeons to focus on the surgical site without dividing his or her attention between the patient and an overhead monitor. It further provides natural and intuitive hand-eye coordination as the surgeons have the ability to look virtually through the abdomen wall.

Camera Design and Implementation

Due to the millimeter-scale size, multiple unobtrusive units are attached throughout the cavity giving surgeons multiple views of the operating area or, with additional image processing, the substantial benefit of advanced cavity visualization without significant overhead on operating preparation time.

Though having multiple cameras placed within the operating cavity will decrease the spatial presence during LESS surgery, for example, its spectral presence will increase due to multiple simultaneous control and video wireless links This problem is overcome by using simple frequency division multiple-access (FDMA) to divide the signals across the available spectrum.

In an embodiment, to allow concurrent use, each MARVEL platform will be designed specifically for one of the ISM bands to transmit its signal across the wireless channel. Multiple receivers will be used to capture each of the transmitted signals.

Panoramic Virtual View Generating and Projecting System

To allow surgeons to specify viewpoint, a view morphing algorithm is used that takes two images from two different viewpoints and generates a new image according to a user specified virtual viewpoint. To use projectors to project videos on an abdomen wall that is convex without distortion, a projector-camera test-bed is used to compensate the geometric distortion on a simulated abdomen wall.

The video taken by the cameras may not be from the viewpoint the surgeons wants to look from. To provide a video from any arbitrary desired viewpoint, a view morphing technique [Seitz and Dyer 1996, Seitz 1997, Loop and Zhang 1999] is used to generate a new video from the actual videos taken by the cameras.

Figure 6:
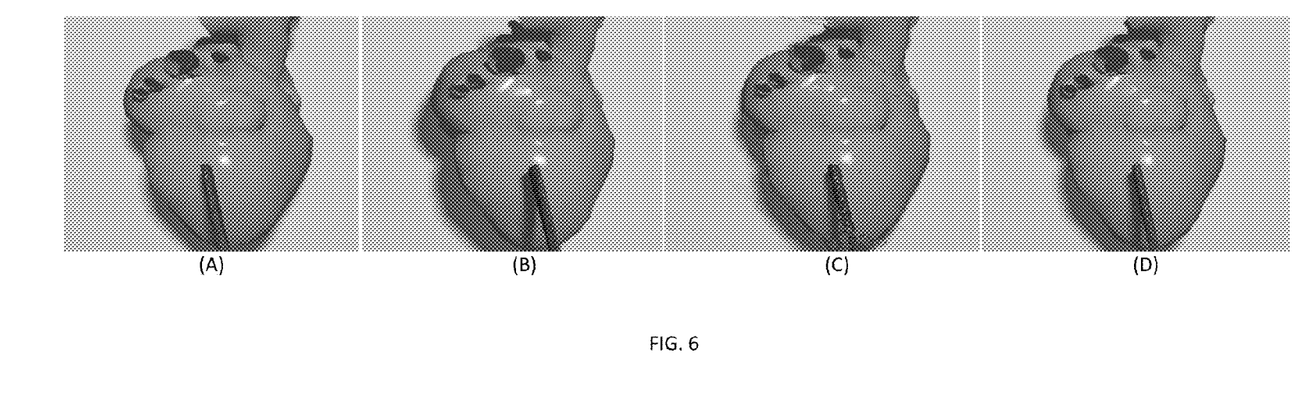
FIG. 6 illustrates a morphing technique.

FIGS. 6A-6D illustrates the ability to change viewpoint of the virtual camera as necessary. FIGS. 6A-6D depict a modeled human heart probed by an instrument, using the Persistence of Vision (POV) Raytracer software package [POV-Ray], with two cameras located at (−5, 0, −10) and (5, 0, −10) and both looked at the point (0, −1, 0) where the center of the heart is. The rendered images are shown in FIGS. 6A and 6B. With a view morphing algorithm, a new virtual image is generated as taken from a virtual camera. FIG. 6C shows one example when the virtual viewpoint is at (0, 0, −10). To verify the result, FIG. 6D shows a real image taken at the expected virtual camera position with POV Raytracer. As shown in the figures, the view morphing result provides a realistic representation with the correct point-of-view with some noise due to the lack of textures on the smooth CAD model.

Figure 7:
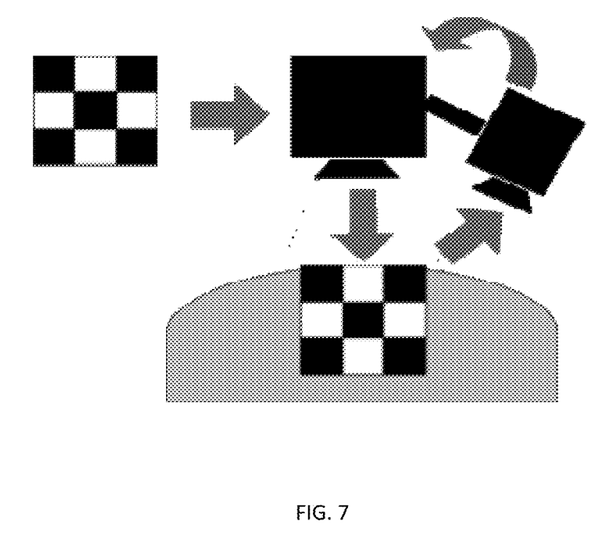
FIG. 7 illustrates a distortion compensation technique.

In addition to view morphing, FIG. 7 depicts the basic idea of a virtually transparent abdomen setup of a scaled down and simplified test-bed. A camera-projector system is setup with a Point Grey Dragonfly 1024×768 resolution color camera and a SVGA projector. The camera provides a distortion feedback, as depicted in FIG. 7. For distortion calibration, the computer sends a checkerboard image to the project and the camera captures the projected checkerboard image. The locations of the checker corners in both images are automatically detected, and then a mapping between the source image and the projected image is built for future use of distortion compensation [Raskar et al. 2003].

Figure 8:
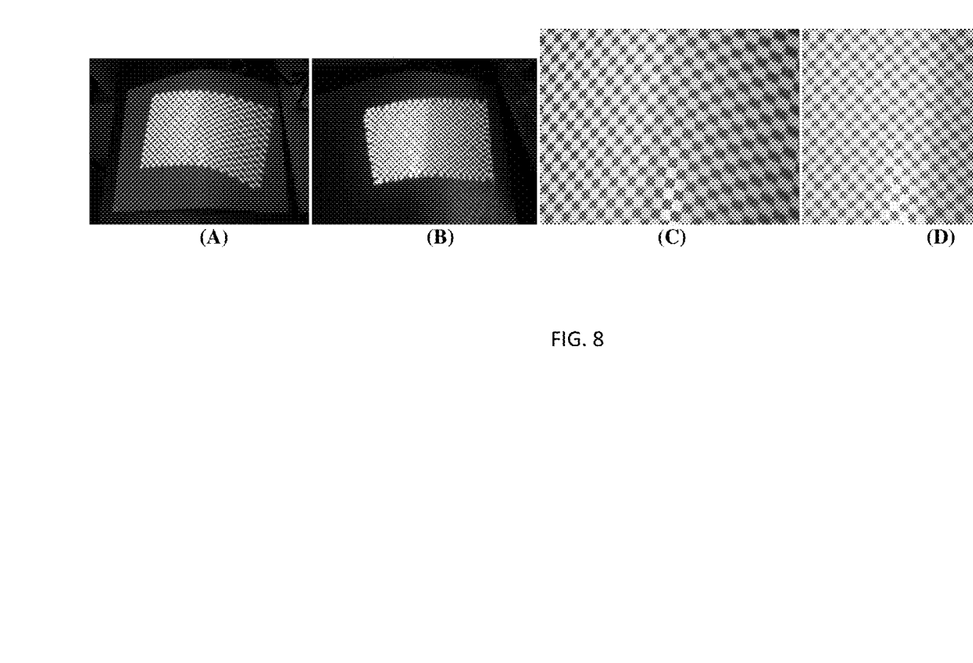
FIG. 8A is a checkerboard displayed on a convex surface without distortion compensation.
FIG. 8B is a checkerboard displayed on a convex surface after distortion compensation.
FIG. 8C is a close up view of 8A.
FIG. 8D is a close up view of 8B.

FIG. 8A shows a checkerboard projected on an abdomen wall dummy The convex shape of the dummy significantly distorts the checkerboard image. FIG. 8B shows the projection of the same checkerboard after geometrical distortion compensation. Most of the distortions at the center area have been corrected. The boundary edge distortion is due to boundary interpretation artifacts that can be masked off. FIGS. 8C and 8D show a close look at the center areas of both uncorrected and corrected display results.

Panoramic Virtual View Generating and Projecting System

As stated, four 1080i HD projectors are mounted above the surgical area with a Point Grey Bumblebee stereo camera mounted in the middle. The Bumblebee stereo camera is calibrated out-of-box providing for a facilitated setup. The projectors and the relative position of the projectors are calibrated with the stereo camera [Raskar and Beardsley 2001]. To obtain the camera pose, three passive optical markers are attached at each needle holder. The Bumblebee stereo camera measures the locations of the optical markers with high accuracy. The position and orientation of the cameras can is estimated from the position of the three optical markers.

Figure 9:
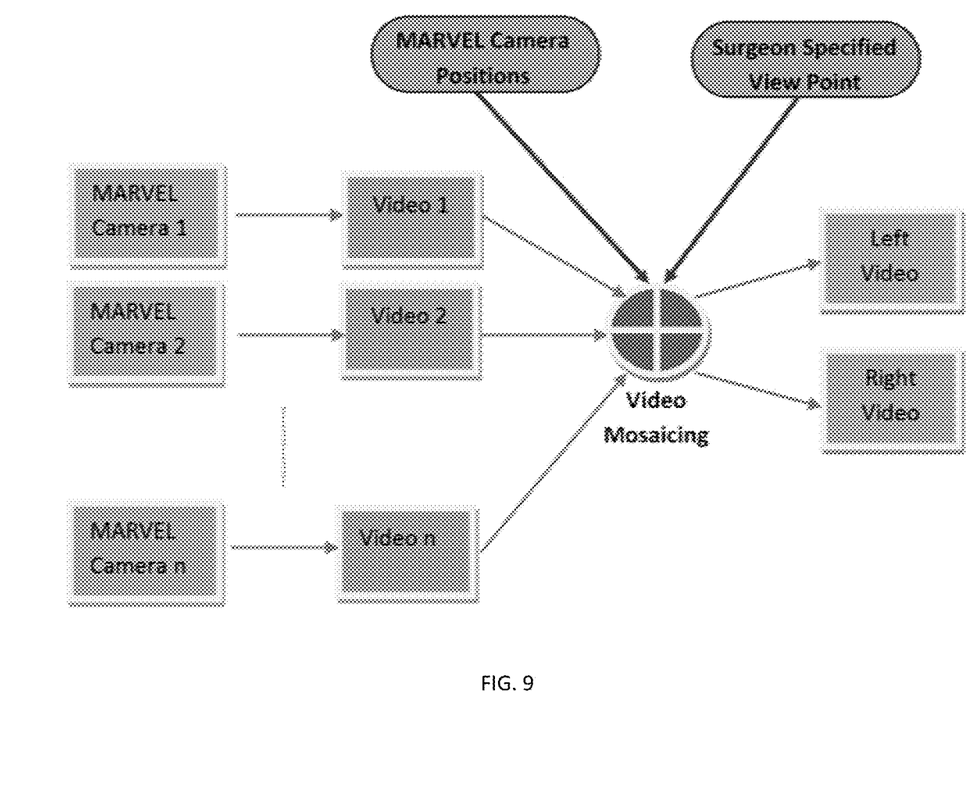
FIG. 9 is a flow chart to generate a 3D panoramic virtual view.

As shown in FIG. 9, the videos from the cameras are first processed with mosaicing techniques [Szeliski 2005]. In computer vision, image mosaicing techniques are well-established and are popular techniques for the visual scene representation applications such as virtual travel and walkthroughs. A number of techniques have been developed for capturing panoramic images of real-world scenes since the 1980s [Lucas and Kanade 1981, Greene 1986]. Images taken at different locations must be aligned and composited into complete panoramic images using an image mosaic or stitching algorithm [Shum 2002]. The mosaicing techniques are widely used in today's digital maps and satellite photos. Every digital camera currently being sold has mosaicing techniques embedded and ready to create ultra wide-angle panoramas right out of box. For endoscope applications, many image mosaicing algorithms have been developed to automatically stitch endoscopic video sequences [Seshamani2006, Konen2006]. A detailed review and tutorial can be found in Ref. [Szeliski 2005].

For this system, since it has the ability to localize the cameras, the stitching algorithm can be carried out much faster and more reliably. For an overview display, the image plan of the center camera is defined as the compositing viewing surface (base image plane) to assembly all the image mosaics. In an embodiment, the global and local alignment algorithm in Ref. [Shum2002] is used since the nominal intrinsic parameters of the cameras are predefined and the extrinsic parameters can be estimated from the Point Grey Stereo camera.

The panoramic video is fed to an overhead monitor to display as in current operating rooms (OR). It may be projected right on the surgery area. In LESS surgery, for example, the display of the internal surgery action on the exterior abdomen wall provides a see-through effect, which is a valuable add-on to the current display system in the operating rooms. The surgical tools above the display area will not block the projection since the multi-projector system projects from different directions [Sukthankar 2001].

Figure 10:
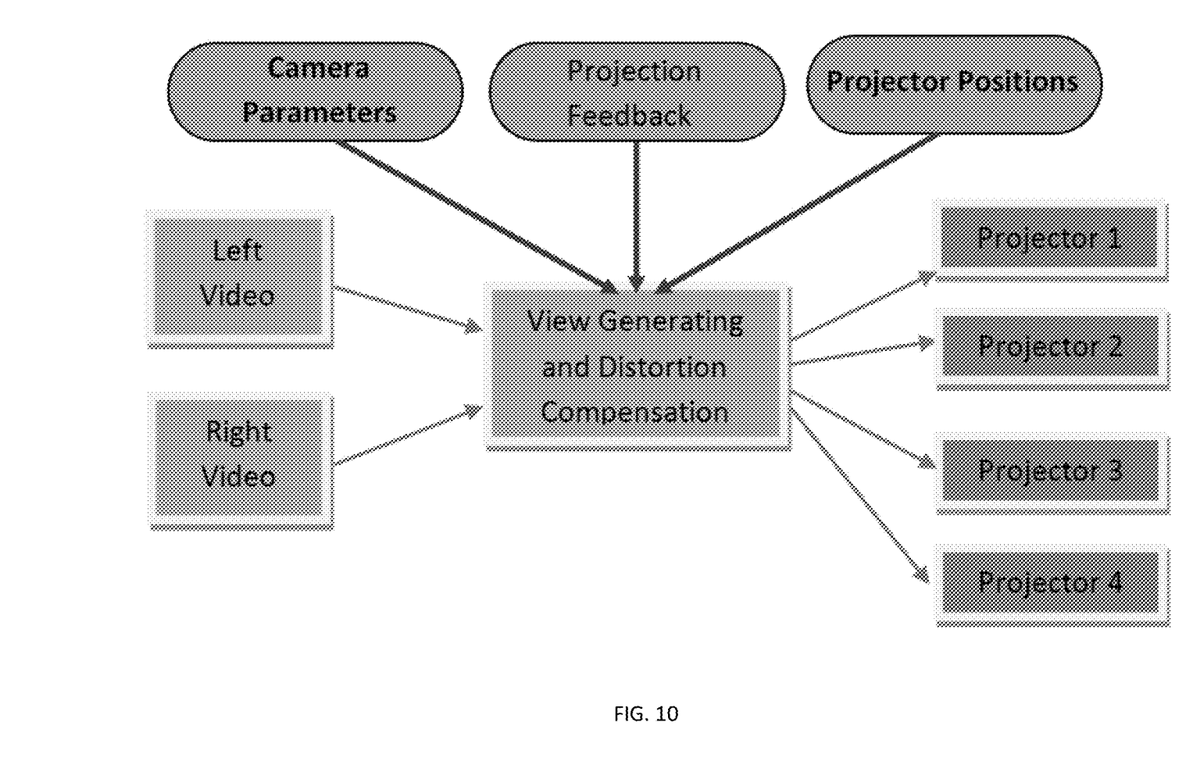
FIG. 10 is a flow chart for view generating and projection distortion compensation.

As shown in FIG. 10, to allow surgeons to specify a viewpoint that is not aligned with any of the camera viewpoints, a view morphing technique is applied as previously described. For stereo display, a pair of images from two parallel virtual viewpoints is generated. For surface distortion compensation, the color of the skin can be measured with the Bumblebee camera and a color compensation algorithm [Fujii 2005] applied to process the video before sending to the projectors. The corrected image is processed for multiple projectors with projection alignment technique [Lyon 1985, Sukthankar 2001].

The left and right video generated by view morphing can be displayed on a commercialized 3D monitor or directly on the patient to have the relations between 3D anatomical structures and the patient be fully appreciated. However, due to the cumbrousness of activate shutter 3D goggles, surgeons try to avoid using them. The only practical other option are polarized glasses. However, the screen has to be silver-coated for best effect. To solve this, the abdomen wall may be covered with polarized screen without interfering with the surgery (e.g. sterilization).

Surgeon Camera Interaction (SCI) System

A pointing gesture will be recognized by the Bumblebee stereo camera with a gesture recognition algorithm [Malik 2004, Agarwal2007] when a surgeon's hand is above the cameras. The 3D location of a fingertip is tracked [Sun 2007, 2008, 2009, Takao 2003]. A tapping behavior is detected when the 3D position of the fingertip is aligned with the location of a camera or on the abdomen surface. Then the tapping location is sent to the panoramic virtual view generating and projecting system to generate a desired view.

The panoramic virtual view generating and projecting system as an additional display provides correct hand-eye coordination and organ and tool localization visual feedback which would significantly benefit MIS training and demonstration to reduce training time. Moreover, it reduces the skill threshold to be sucessful in MIS and reduces operating time by enableing the surgeons to focus on the surgical site without dividing his or her attention between the patient and an overhead monitor. It regains the visual benefit of open surgery. Surgeons will operate as if they were looking directly into the body cavity through a transparent epidermis and tissue layer.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A method of projecting images of internal structures externally on skin of a body of a patient, comprising:
   positioning, through a surgical site, a plurality of wireless image capture devices along an internal cavity of the body;
   attaching the plurality of image capture devices along the internal cavity;
   transmitting unprocessed images from the plurality of image capture devices to a processing unit;
   morphing, using the processing unit, the unprocessed images, and generating a modified image based at least in part on the morphed unprocessed images, wherein the modified image includes surgical anatomy and surgical instruments located in the body;
   projecting, using a projector associated with the processing unit, the modified image externally on the skin; and
   aligning the modified image on the skin to correspond with at least one of a physical location, an orientation or a size of at least one of the surgical anatomy or the surgical instruments located in the body.

2. The method of claim 1, further comprising correcting, using the processing unit, the modified image for color distortion.

3. The method of claim 1, further comprising correcting, using the processing unit, the modified image for geometrical distortion based at least in part on feedback from a stereo camera.

4. The method of claim 1, wherein at least one of the plurality of wireless image capture devices includes a light source.

5. The method of claim 1, wherein attaching at least one of the plurality of image capture devices to the internal cavity includes affixing the at least one image capture device to the internal cavity using a set of needles.

6. The method of claim 5, wherein the set of needles provide power to the at least one image capture device.

7. The method of claim 1, wherein aligning the modified image includes estimating alignment based at least in part on respective optical markers associated with the plurality of wireless image capture devices.

8. The method of claim 1, wherein projecting the modified image externally on the skin includes projecting the modified image using the projector and a stereo camera.

9. The method of claim 8, further comprising calibrating a relative position of the projector with the stereo camera.

10. The method of claim 1, wherein projecting the modified image externally on the skin includes projecting the modified image on the patient's skin in three dimensions.

11. The method of claim 10, further comprising recognizing a set of gestures of a surgeon and detecting a viewpoint of a surgeon based at least in part on the set of gestures.

12. A system for projecting images of internal structures externally on skin of a body of a patient, comprising:
    a plurality of wireless cameras adapted to be anchored to a cavity wall of the patient;
    a processing unit that generates a modified image based at least in part on a set of images received from the plurality of wireless cameras; and
    a projection system adapted to project the modified image externally on the skin of the patient, wherein the projection system is comprised of a projector and a stereo camera.

13. The system of claim 12, further comprising a surgeon-camera interface that enables a surgeon to specify a desired viewing point.

14. The system of claim 13, wherein the surgeon-camera interface includes a gesture recognition unit that tracks a viewpoint of the surgeon.

15. The system of claim 12, wherein at least one of the cameras included in the plurality of wireless cameras is anchored by a set of needles.

16. The system of claim 15, wherein at least one of the cameras included in the plurality of wireless cameras includes a light source.

17. The system of claim 12, wherein the processing unit employs image stitching to generate the modified image.

18. The system of claim 12, wherein the processing unit compensates for color distortion.

19. The system of claim 12, wherein the processing unit corrects geometrical distortion based at least in part on feedback from the stereo camera.

20. The system of claim 12, wherein the projection system is mounted externally above the surgical site.

* * * * *